(12) United States Patent
Payne et al.

(10) Patent No.: US 9,733,258 B2
(45) Date of Patent: Aug. 15, 2017

(54) BIOMARKER FOR DETERMINING MITOCHONDRIAL DAMAGE IN FRIEDREICH'S ATAXIA

(71) Applicant: Indiana University Research and Technology Corporation, Indianapolis, IN (US)

(72) Inventors: R. Mark Payne, Zionsville, IN (US); Gregory R. Wagner, Indianapolis, IN (US); Clifford M. Babbey, Indianapolis, IN (US); P. Melanie Pride, Indianapolis, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 0 days.

(21) Appl. No.: 14/382,367

(22) PCT Filed: Mar. 1, 2013

(86) PCT No.: PCT/US2013/028609
§ 371 (c)(1),
(2) Date: Sep. 2, 2014

(87) PCT Pub. No.: WO2013/130964
PCT Pub. Date: Sep. 6, 2013

(65) Prior Publication Data
US 2015/0132769 A1 May 14, 2015

Related U.S. Application Data

(60) Provisional application No. 61/605,783, filed on Mar. 2, 2012, provisional application No. 61/607,918, filed on Mar. 7, 2012.

(51) Int. Cl.
| | |
|---|---|
| *A61K 38/00* | (2006.01) |
| *C07K 16/00* | (2006.01) |
| *G01N 33/68* | (2006.01) |
| *G01N 33/48* | (2006.01) |
| *G01N 33/50* | (2006.01) |
| *G01N 33/573* | (2006.01) |
| *C12Q 1/32* | (2006.01) |

(52) U.S. Cl.
CPC .......... *G01N 33/6893* (2013.01); *C12Q 1/32* (2013.01); *G01N 33/48* (2013.01); *G01N 33/50* (2013.01); *G01N 33/5079* (2013.01); *G01N 33/5735* (2013.01); *G01N 33/68* (2013.01); *G01N 2440/10* (2013.01); *G01N 2500/02* (2013.01); *G01N 2800/285* (2013.01); *G01N 2800/52* (2013.01)

(58) Field of Classification Search
None
See application file for complete search history.

(56) References Cited

U.S. PATENT DOCUMENTS

2010/0209427 A1 8/2010 Li et al.

FOREIGN PATENT DOCUMENTS

| WO | 2007133689 A2 | 11/2007 |
| WO | 2008073162 A2 | 6/2008 |

OTHER PUBLICATIONS

Ahn, B.-H., Kim, H.-S., Song, S., Lee, I.H., Liu, J., Vassilopoulos, A., Deng, C.-X. and Finkel, T. (2008) A role for the mitochondrial deacetylase Sirt3 in regulating energy homeostasis. Proc Natl Acad Sci U S A, 105, 14447-14452.
Blander, G. and Guarente, L. (2004) The Sir2 family of protein deacetylases. Annual Review of Biochemistry, 73, 417-435.
Brown, M.D., Voljavec, A.S., Lott, M.T., MacDonald, I. and Wallace, D.C. (1992) Leber's hereditary optic neuropathy: a model for mitochondrial neurodegenerative diseases. FASEB J, 6, 2791-2799.
Bulteau, A.-L., O'Neill, H.A., Kennedy, M.G., Ikeda-Saito, M., Isaya, G. and Szweda, L.I. (2004) Frataxin Acts as an Iron Chaperone Protein to Modulate Mitochondrial Aconitase Activity. Science, 305, 242-245.
Campuzano, V., Montermini, L., Molto, M.D., Pianese, L., Cossee, M., Cavalcanti, F., Monros, E., Rodius, F., Duclos, F., Monticelli, A. et al. (1996) Friedreich's ataxia: autosomal recessive disease caused by an intronic GAA triplet repeat expansion. Science, 271, 1423-1427.
Cimen, H., Han, M.J., Yang, Y., Tong, Q., Koc, H. and Koc, E.C. (2010) Regulation of succinate dehydrogenase activity by SIRT3 in mammalian mitochondria. Biochemistry, 49, 304-311.
Crowley, K.S. and Payne, R.M. (1998) Ribosome Binding to Mitochondria Is Regulated by GTP and the Transit Peptide. J Biol Chem, 273, 17278-17285.
Durr, A., Cossee, M., Agid, Y., Campuzano, V., Mignard, C., Penet, C., Mandel, J.-L., Brice, A. and Koenig, M. (1996) Clinical and Genetic Abnormalities in Patients with Friedreich's Ataxia. N Engl J Med, 335, 1169-1175.
Emond, M., Lepage, G., Vanasse, M. and Pandolfo, M. (2000) Increased levels of plasma malondialdehyde in Friedreich ataxia. Neurology, 55, 1752-1753.
Fan, W., Waymire, K.G., Narula, N., Li, P., Rocher, C., Coskun, P.E., Vannan, M.A., Narula, J., Macgregor, G.R. and Wallace, D.C. (2008) A mouse model of mitochondrial disease reveals germline selection against severe mtDNA mutations. Science, 319, 958-962.
Finley, L.W., Carracedo, A., Lee, J., Souza, A., Egia, A., Zhang, J., Teruya-Feldstein, J., Moreira, P.I., Cardoso, S.M., Clish, C.B. et al. (2011) SIRT3 opposes reprogramming of cancer cell metabolism through HIF1alpha destabilization. Cancer Cell, 19, 416-428.

(Continued)

*Primary Examiner* — Olga N Chernyshev
(74) *Attorney, Agent, or Firm* — Stinson Leonard Street LLP

(57) ABSTRACT

Compositions and methods for screening for a disease or a disorder associated with a deficiency in frataxin in a subject using biomarkers for diseases or disorders associated with a deficiency in frataxin are disclosed. The compositions and methods include determining the acetylation status of mitochondrial proteins. Also disclosed are methods of detecting progression of a disease or a disorder associated with a deficiency in frataxin in a subject and methods of monitoring effectiveness of a therapy for diseases or disorders associated with a deficiency in frataxin.

2 Claims, 10 Drawing Sheets

(56) References Cited

OTHER PUBLICATIONS

Fritz, K.S., Galligan, J.J., Smathers, R.L., Roede, J.R., Shearn, C.T., Reigan, P. and Petersen, D.R. (2011) 4-Hydroxynonenal inhibits SIRT3 via thiol-specific modification. Chemical research in toxicology, 24, 651-662.
Guarente, L. (2011) The logic linking protein acetylation and metabolism. Cell Metabolism, 14, 151-153.
Hafner, A.V., Dai, J., Gomes, A.P., Xiao, C.Y., Palmeira, C.M., Rosenzweig, A. and Sinclair, D.A. (2010) Regulation of the mPTP by SIRT3-mediated deacetylation of CypD at lysine 166 suppresses age-related cardiac hypertrophy. Aging (Albany NY), 2, 914-923.
Hallows, W.C., Lee, S. and Denu, J.M. (2006) Sirtuins deacetylate and activate mammalian acetyl-CoA synthetases. Proc Natl Acad Sci U S A, 103, 10230-10235.
Hebert, A.S., et al., "Calorie Restriction and SIRT3 Trigger Global Reprogramming of the Mitochondrial Protein Acetylome", Mol. Cell. 49:186-199 (2013).
Hirschey, M.D., Shimazu, T., Goetzman, E., Jing, E., Schwer, B., Lombard, D.B., Grueter, C.A., Harris, C., Biddinger, S., Ilkayeva, O.R. et al. (2010) SIRT3 regulates mitochondrial fatty-acid oxidation by reversible enzyme deacetylation. Nature, 464, 121-125.
Kim, H.S., Patel, K., Muldoon-Jacobs, K., Bisht, K.S., Aykin-Burns, N., Pennington, J.D., van der Meer, R., Nguyen, P., Savage, J., Owens, K.M. et al. (2010) SIRT3 is a mitochondria-localized tumor suppressor required for maintenance of mitochondrial integrity and metabolism during stress. Cancer Cell, 17, 41-52.
Kim, S.C., Sprung, R., Chen, Y., Xu, Y., Ball, H., Pei, J., Cheng, T., Kho, Y., Xiao, H., Xiao, L. et al. (2006) Substrate and functional diversity of lysine acetylation revealed by a proteomics survey. Mol Cell, 23, 607-618.
Krebs, H.A. and Veech, R.L. (1969) Equilibrium relations between pyridine nucleotides and adenine nucleotides and their roles in the regulation of metabolic processes. Advances in enzyme regulation, 7, 397-413.
Lodi, R. Cooper, J.M. Bradley, J.L., Manners, D., Styles, P., Taylor, D.J. and Schapira, A.H. (1999) Deficit of in vivo mitochondrial ATP production in patients with Friedreich ataxia. Proc Natl Acad Sci U S A, 96, 11492-11495.
Lombard et al., "Mammalian Sir2 homolog SIRT3 regulates global mitochondrial lysine acetylation." Molecular and Cellular Biology, vol. 27, No. 24, pp. 8807-8814 (Oct. 8, 2007).
Lowry, O.H., Passonneau, J.V. and Rock, M.K. (1961) The stability of pyridine nucleotides. J. Biol. Chem., 236, 2756-2759.
Lowry, O.H., Passonneau, J.V., Schulz, D.W. and Rock, M.K. (1961) The measurement of pyridine nucleotides by enzymatic cycling. J. Biol. Chem., 236, 2746-2755.
Mayevsky, A. and Rogatsky, G.G. (2007) Mitochondrial function in vivo evaluated by NADH fluorescence: from animal models to human studies. American journal of physiology. Cell physiology, 292, C615-640.
Munnich, A., Rustin, P., Rotig, A., Chretien, D., Bonnefont, J.P., Nuttin, C., Cormier, V., Vassault, A., Parvy, P., Bardet, J. et al. (1992) Clinical Aspects of Mitochondrial Disorders. Journal of inherited metabolic disease, 15, 448-455.
Narula, N., Zaragoza, M.V., Sengupta, P.P., Li, P., Haider, N., Verjans, J., Waymire, K., Vannan, M. and Wallace, D.C. (2011) Adenine nucleotide translocase 1 deficiency results in dilated cardiomyopathy with defects in myocardial mechanics, histopathological alterations, and activation of apoptosis. JACC Cardiovasc Imaging, 4, 1-10.
Punga, T. and Buhler, M. (2010) Long intronic GAA repeats causing Friedreich ataxia impede transcription elongation. EMBO Mol Med, 2, 120-129.
Qiu, X., Brown, K., Hirschey, M.D., Verdin, E. and Chen, D. (2010) Calorie restriction reduces oxidative stress by SIRT3-mediated SOD2 activation. Cell Metab, 12, 662-667.
Rotig, A., de Lonlay, P., Chretien, D., Foury, F., Koenig, M., Sidi, D., Munnich, A. and Rustin, P. (1997) Aconitase and mitochondrial iron-sulphur protein deficiency in Friedreich ataxia. Nat Genet, 17, 215-217.

Schmidt, M.T., Smith, B.C., Jackson, M.D. and Denu, J.M. (2004) Coenzyme specificity of Sir2 protein deacetylases: implications for physiological regulation. The Journal of biological chemistry, 279, 40122-40129.
Schmucker, S. and Puccio, H. (2010) Understanding the molecular mechanisms of Friedreich's ataxia to develop therapeutic approaches. Human molecular genetics, 19, R103-110.
Schwer, B., Bunkenborg, J., Verdin, R.O., Andersen, J.S. and Verdin, E. (2006) Reversible lysine acetylation controls the activity of the mitochondrial enzyme acetyl-CoA synthetase 2. Proc Natl Acad Sci U S A, 103, 10224-10229.
Schwer, B., Eckersdorff, M., Li, Y., Silva, J.C., Fermin, D., Kurtev, M.V., Giallourakis, C., Comb, M.J., Alt, F.W. and Lombard, D.B. (2009) Calorie restriction alters mitochondrial protein acetylation. Aging Cell, 8, 604-606.
Shimazu, T., Hirschey, M.D., Hua, L., Dittenhafer-Reed, K.E., Schwer, B., Lombard, D.B., Li, Y., Bunkenborg, J., Alt, F.W., Denu, J.M. et al. (2010) SIRT3 deacetylates mitochondrial 3-hydroxy-3-methylglutaryl CoA synthase 2 and regulates ketone body production. Cell Metab, 12, 654-661.
Sliwa, D., Dairou, J., Camadro, J.M. and Santos, R. (2011) Inactivation of mitochondrial aspartate aminotransferase contributes to the respiratory deficit of yeast frataxin-deficient cells. The Biochemical journal.
Someya, S., Yu, W., Hallows, W.C., Xu, J., Vann, J.M., Leeuwenburgh, C., Tanokura, M., Denu, J.M. and Prolla, T.A. (2010) Sirt3 mediates reduction of oxidative damage and prevention of age-related hearing loss under caloric restriction. Cell, 143, 802-812.
Sundaresan, N.R., Gupta, M., Kim, G., Rajamohan, S.B., Isbatan, A. and Gupta, M.P. (2009) Sirt3 blocks the cardiac hypertrophic response by augmenting Foxo3a-dependent antioxidant defense mechanisms in mice. J Clin Invest, 119, 2758-2771.
Sundaresan, N.R., Samant, S.A., Pillai, V.B., Rajamohan, S.B. and Gupta, M.P. (2008) SIRT3 Is a Stress-Responsive Deacetylase in Cardiomyocytes That Protects Cells from Stress-Mediated Cell Death by Deacetylation of Ku70. Mol Cell Biol, 28, 6384-6401.
Sung, H.J., Ma, W., Wang, P.Y., Hynes, J., O'Riordan, T.C., Combs, C.A., McCoy, J.P., Jr., Bunz, F., Kang, J.G. and Hwang, P.M. (2010) Mitochondrial respiration protects against oxygen-associated DNA damage. Nature communications, 1, 5.
Sutak, R., Xu, X., Whitnall, M., Kashem, M.A., Vyoral, D. and Richardson, D.R. (2008) Proteomic analysis of hearts from frataxin knockout mice: marked rearrangement of energy metabolism, a response to cellular stress and altered expression of proteins involved in cell structure, motility and metabolism. Proteomics, 8, 1731-1741.
Tao, R., Coleman, M.C., Pennington, J.D., Ozden, O., Park, S.H., Jiang, H., Kim, H.S., Flynn, C.R., Hill, S., Hayes McDonald, W. et al. (2010) Sirt3-Mediated Deacetylation of Evolutionarily Conserved Lysine 122 Regulates MnSOD Activity in Response to Stress. Mol Cell, 40, 893-904.
Tsai, C.L. and Barondeau, D.P. (2010) Human frataxin is an allosteric switch that activates the Fe—S cluster biosynthetic complex. Biochemistry, 49, 9132-9139.
Ventura-Clapier, R., Gamier, A. and Veksler, V. (2004) Energy metabolism in heart failure. J Physiol, 555, 1-13.
Verdin, E., Hirschey, M.D., Finley, L.W. and Haigis, M.C. (2010) Sirtuin regulation of mitochondria: energy production, apoptosis, and signaling. Trends Biochem Sci, 35, 669-675.
Vyas et al., Hum. Mol. Genet. 2012, 21(6):1230-1247.
Vyas, P.M., Tomamichel, W.J., Pride, P.M., Babbey, C.M., Wang, Q., Mercier, J., Martin, E.M. and Payne, R.M. (2011) A TAT-Frataxin fusion protein increases lifespan and cardiac function in a conditional Friedreich's ataxia mouse model. Human molecular genetics, in press.
Wagner et al., "Friedreich's ataxia reveals a mechanism for coordinate regulation of oxidative metabolism via feedback inhibition of the SIRT3 deacetylase." Human Molecular Genetics, vol. 21, No. 12, pp. 2688-2697 (Mar. 6, 2012).
Wagner, G.R. and Payne, R.M. (2011) Mitochondrial acetylation and diseases of aging. J Aging Res, 2011, 234875.

(56) References Cited

OTHER PUBLICATIONS

Wallace, D.C. (2005) A mitochondrial paradigm of metabolic and degenerative diseases, aging, and cancer: a dawn for evolutionary medicine. Annual review of genetics, 39, 359-407.

Watmough, N.J., Bindoff, L.A., Birch-Machin, M.A., Jackson, S., Bartlett, K., Ragan, C.I., Poulton, J., Gardiner, R.M., Sherratt, H.S. and Turnbull, D.M. (1990) Impaired mitochondrial beta-oxidation in a patient with an abnormality of the respiratory chain. Studies in skeletal muscle mitochondria. The Journal of Clinical Investigation, 85, 177-184.

Zhang, J., Sprung, R., Pei, J., Tan, X., Kim, S., Zhu, H., Liu, C.F., Grishin, N.V. and Zhao, Y. (2009) Lysine acetylation is a highly abundant and evolutionarily conserved modification in *Escherichia coli*. Molecular & cellular proteomics : MCP, 8, 215-225.

Zhao, S., Xu, W., Jiang, W., Yu, W., Lin, Y., Zhang, T., Yao, J., Zhou, L., Zeng, Y., Li, H. et al. (2010) Regulation of cellular metabolism by protein lysine acetylation. Science, 327, 1000-1004.

International Search Report and Written Opinion for Application No. PCT/US2013/028609 dated Jun. 18, 2013.

FIG. 6
FIG. 7
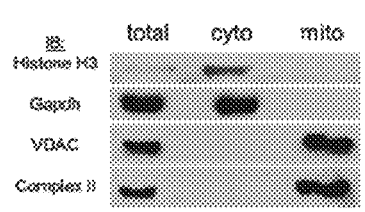
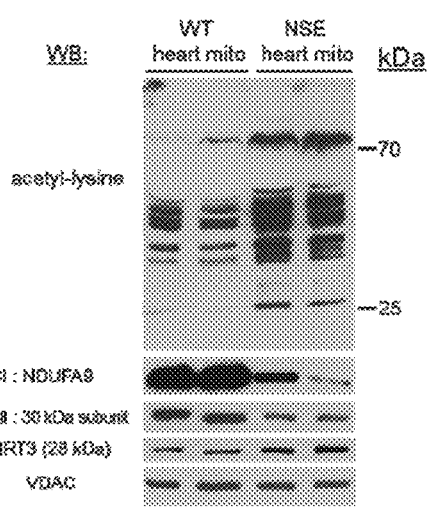
FIG. 8
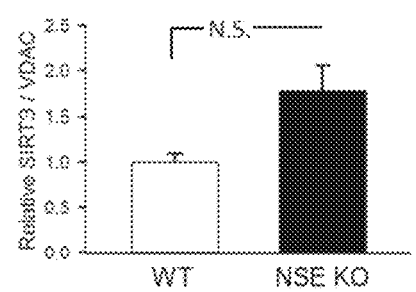

BIOMARKER FOR DETERMINING MITOCHONDRIAL DAMAGE IN FRIEDREICH'S ATAXIA

CROSS-REFERENCE TO RELATED APPLICATIONS

This application claims priority to International Publication Number WO 2013/130964, filed on Mar. 1, 2013, which claims priority to U.S. provisional patent application No. 61/605,783 filed on Mar. 2, 2012 and U.S. Provisional application No. 61/607,918, filed on Mar. 7, 2012, which are incorporated herein by reference in their entireties.

STATEMENT OF GOVERNMENT SUPPORT

This invention was made with government support under HL085098 awarded by the National Institutes of Health. The government has certain rights in the invention.

BACKGROUND OF THE DISCLOSURE

The present disclosure relates generally to compositions and methods for screening for diseases or disorders associated with a deficiency in frataxin. More particularly, the present disclosure relates to methods of screening for a disease or disorder associated with a deficiency in frataxin, as well as methods of screening for therapeutic agents for use in treating a disease or disorder associated with a deficiency in frataxin, or damage from reactive oxygen species to mitochondrial proteins affecting the respiratory chain, or increased mitochondrial protein acetylation affecting mitochondrial function, as well as method of screening for therapeutic agents for use in treating a disease or disorder associated with a deficiency in frataxin.

Friedreich's Ataxia (FRDA) is an autosomal recessive mitochondrial disorder caused by a homozygous triplet nucleotide repeat (GAA·TTC) expansion in intron 1 of the FXN gene located on chromosome 9q21.11. This intronic expansion causes impaired transcription of the FXN gene and, consequently, a pathological deficiency of the FXN gene product, frataxin. Frataxin is targeted to the mitochondrial matrix, where it is known to act as an iron-binding protein and participates in the proper assembly and function of iron-sulfur cluster (ISC) dependent proteins including complexes I, II, and III of the respiratory chain and aconitase of the tricarboxylic acid (TCA) cycle. Thus, frataxin deficiency severely compromises both cellular respiration and overall mitochondrial function leading to energetic stress and ATP deficiency. Although patients develop multisystem disease including early spinocerebellar degeneration, ataxia, and diabetes, the primary cause of death is heart failure for nearly 85% of those afflicted. Similarly, although the phenotypes of the neuron-specific enolase (NSE) and muscle creatine kinase (MCK) Cre conditional mouse models of FRDA differ, both models develop a fatal cardiomyopathy and impaired activity of iron-sulfur cluster-dependent respiratory complexes consistent with the human disease.

Recent work has demonstrated that lysine acetylation is a highly conserved and abundant post-translational modification within mitochondria that is responsive to nutrient availability and may contribute to the physiological adaptations of reduced caloric intake. Multiple investigations have demonstrated a role for reversible mitochondrial enzyme deacetylation and, specifically, the $NAD^+$-dependent deacetylase SIRT3, in the regulation of fatty acid oxidation, the TCA cycle, electron transport via respiratory complexes I and II, and overall oxidative metabolism. SIRT3-mediated deacetylation has recently emerged as a major mechanism regulating the activity of mitochondrial oxidative and intermediary metabolism. SIRT3 is also uniquely poised to respond to the flux of mitochondrial $NAD^+$ and NADH, which is determined, in large part, by the capacity of the respiratory chain to oxidize NADH. This capacity is severely decreased in FRDA, as well as in other mitochondrial defects such as cytochrome c oxidase (complex IV) deficiency, causing an accumulation of NADH and, consequently, a redox state of perceived nutrient excess.

Defects in cellular respiration may be inherited as mitochondrial disease, or acquired over a lifetime via somatic mutations, and are linked to many conditions including neurodegenerative disease, diabetes, heart failure, cancer and in the aging process in general. The involvement of cellular respiration in numerous common human pathologies emphasizes the need for greater understanding of the pathophysiological processes that occur in response to respiratory chain compromise. Accordingly, there exists a need to develop biomarkers of diseases or disorders associated with a deficiency in frataxin.

SUMMARY OF THE DISCLOSURE

The present disclosure relates generally to methods and kits for screening for diseases and disorders associated with a deficiency in frataxin. More particularly, it has been discovered that the loss of frataxin in mitochondria causes the progressive hyperacetylation of mitochondrial proteins. Accordingly, the present disclosure is directed to methods for screening for diseases and disorders associated with a deficiency in frataxin, as well as to a kit for measuring or detecting protein acetylation levels. Additionally, the present disclosure is directed to methods for detecting the progression of a disease or disorder associated with a deficiency in frataxin in a subject having or suspected of having a deficiency in frataxin and to methods for monitoring the effectiveness of therapy in a subject having or suspected of having a disease or disorder associated with a deficiency in frataxin. The present disclosure also is directed to methods of screening for therapeutic agents for use in treating diseases and disorders associated with a deficiency in frataxin.

In one aspect, the present disclosure is directed to a method of screening for a deficiency in frataxin in a subject. The method includes determining the acetylation status of a mitochondrial protein in a sample tissue and determining the acetylation status of a mitochondrial protein in a normal tissue. An increase in acetyl-lysine in the sample tissue as compared to acetyl-lysine in the normal tissue is indicative of a deficiency in frataxin.

In another aspect, the present disclosure is directed to a method of screening for a deficiency in frataxin in a subject. The method includes determining the mitochondrial NADH level in a sample tissue and determining the mitochondrial NADH level in a normal tissue. An increase in the NADH level in the sample tissue as compared to the NADH level in the normal tissue is indicative of a deficiency in frataxin. In some embodiments, the method further includes determining the mitochondrial $NAD^+$ level in a sample tissue and/or determining the $NAD^+/NADH$ ratio in the sample tissue and determining the mitochondrial $NAD^+$ level in a normal tissue and/or determining $NAD^+/NADH$ ratio in the normal tissue, wherein a decrease in the $NAD^+/NADH$ ratio in the sample tissue as compared to the $NAD^+/NADH$ ratio in the normal tissue is indicative of a deficiency in frataxin.

In another aspect, the present disclosure is directed to a kit for measuring levels of mitochondrial protein acetylation. The kit includes an arm-acetyl-lysine-specific antibody and an antibody that specifically binds to a mitochondrial protein. The kit may include reagents for processing a sample, for isolating mitochondria, and for detecting protein acetylation levels (e.g., isolation buffers, colorimetric assay buffers and reagents, and acetylation detection buffers and reagents). In one embodiment, the kit measures acetyl-lysine residues with, for example, an acetyl-lysine-specific antibody.

In another aspect, the present disclosure is directed to a method of detecting the progression of a disease or a disorder associated with a deficiency in frataxin. The method includes measuring mitochondrial protein acetylation in an earlier-obtained sample (i.e., a first chronological sample) and a later-obtained chronological sample (i.e., a second chronological sample) from a subject having or suspected of having the disease or the disorder associated with a deficiency in frataxin, where an increase in mitochondrial protein acetylation in the second chronological sample indicates progression of the disease or the disorder when compared to the mitochondrial protein acetylation in the first chronological sample.

In another aspect, the present disclosure is directed to a method for monitoring the effectiveness of therapy in a subject having or suspected of having a deficiency in frataxin. The method includes measuring mitochondrial protein acetylation in at least a first chronological sample, administering the therapy to the subject, and measuring mitochondrial protein acetylation in at least a second chronological sample, where a decrease in the mitochondrial protein acetylation in the second chronological sample when compared to the mitochondrial protein acetylation in the first chronological sample indicates effectiveness of therapy.

In another aspect, the present disclosure is directed to a method for screening for agents that can be used for treating a disease or a disorder associated with a deficiency in frataxin. The method includes measuring mitochondrial protein acetylation in a subject having hyperacetylated mitochondrial proteins, administering an agent suspected of modulating protein acetylation to the subject, measuring mitochondrial protein acetylation after administration of the agent, where the agent is considered to be a candidate for treating the disease or the disorder associated with a deficiency in frataxin if the mitochondrial protein acetylation is decreased in the sample after administration of the agent.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 6 is a Western blot (WB) demonstrating the purity of the cardiac mitochondrial preparations using Histone H3 as a nuclear marker, Gapdh as a cytoplasmic marker, VDAC as a mitochondrial outer membrane marker, and Complex II as a mitochondrial inner membrane marker as discussed in Example 3.

FIG. 7 is a Western blot probing for internal acetyl-lysine residues of isolated mitochondrial protein obtained from hearts from 24 day-old wild-type (WT, n=2, Lanes 1 and 2) hearts and 24 day-old NSE frataxin knockout hearts ("NSE"; n=2, Lanes 3 and 4), Western blots probing for the respiratory Complex I subunit NDUFA9, the Complex II 30 kDa iron-sulfur subunit, SIRT3 and the mitochondrial outer membrane protein voltage-dependent anion channel (VDAC) as a loading control as discussed in Example 3.

FIG. 8 is a graph showing the calculated densitometry for SIRT3 relative to the loading control VDAC shown in FIG. 7 (mean±SD; N.S.: not significant) as discussed in Example 3.

Figure 1:
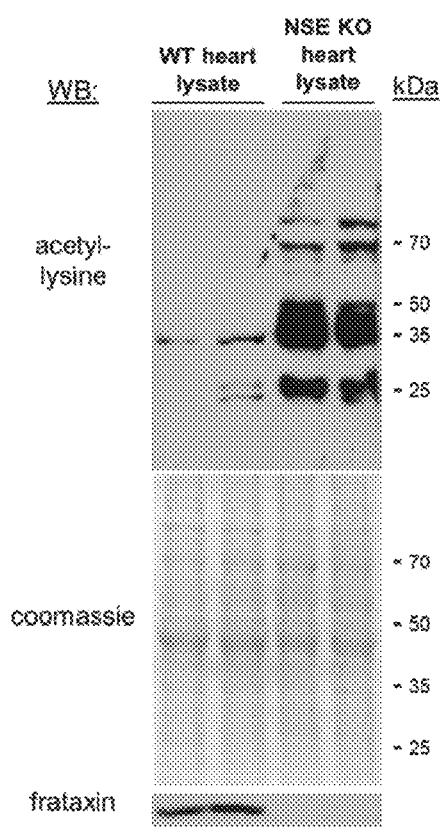
FIG. 1 is a Western blot (WB) probing for internal acetyl-lysine residues using total heart homogenates derived from 24 day-old wild-type (WT, n=2, lanes 1 and 2) and 24 day-old NSE-Cre knockout mice ("NSE KO"; n=2, lanes 3 and 4), the corresponding SDS-PAGE gel stained with Coomassie Blue and a Western blot probing for frataxin as discussed in Example 2.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein may be used in the practice or testing of the present disclosure, the preferred materials and methods are described below.

In accordance with the present disclosure, biomarkers useful for assessing mitochondrial damage in disease have been discovered. Significantly, it has been discovered that a deficiency in frataxin can cause progressive hyperacetylation of mitochondrial proteins. Accordingly, the present disclosure relates to assessing the acetylation status of mitochondrial proteins as biomarkers for assessing mitochondrial damage. Methods for assessing acetylation status of, for example, mitochondrial proteins to determine oxidative damage to mitochondria in certain diseases have also been discovered.)

Suitable methods for determining the acetylation status of a mitochondrial protein may be performed by Western blot analysis, immunoprecipitation, enzyme-linked immunosorbent assay (ELISA) and mass spectrometry.

In another aspect, the present disclosure is directed to a method of screening for a disease or a disorder associated with a deficiency in frataxin in a subject. The method includes determining the acetylation status of a mitochondrial protein, wherein acetyl-lysine in a sample from the subject is increased as compared to acetyl-lysine in normal tissue is indicative of a disease or a disorder associated with a deficiency in frataxin. As used herein, "normal tissue" refers to a reference sample obtained from a subject that is known to not have a disease or a disorder associated with a deficiency in frataxin. The phrase "normal tissue" is also intended to refer to a reference value assigned to a subject or a panel of subjects that are known to not have a disease or a disorder associated with a deficiency in frataxin.

Mitochondria may be isolated by methods for isolating mitochondria from cells known to those skilled in the art. The method may further include sub-fractionation of the tissue sample. Sub-fractionation of the tissue sample allows for the isolation of mitochondria from other cellular and sub-cellular components of the tissue. Any suitable methods known by those skilled in the art may be used for tissue sub-fractionation. For example, tissue may be homogenized and then subjected to a standard differential centrifugation method to initially pellet nuclei and cellular debris followed by centrifugation of the resulting supernatant to pellet mitochondria.

Protein acetylation may be measured by methods for detecting acetylation known to those skilled in the art. A particularly suitable method for detecting protein acetylation may be, for example, by detecting lysine acetylation. In one embodiment, levels of acetyl-lysine may be measured by utilizing an antibody specific for acetyl-lysine residues. Antibodies that specifically bind to acetyl-lysine residues are commercially available (Immunechem, Cell Signaling) or may be made using methods known by those skilled in the art. Suitable methods for detecting lysine acetylation status of a mitochondrial protein can be determined, for example, by Western blot analysis, immunoprecipitation, enzyme-linked immunosorbent assay (ELISA) mass spectrometry and combinations of these methods.

Suitable subjects may be mammals. Particularly suitable mammals can be, for example, humans and rodents such as, for example, rats and mice.

Mitochondrial proteins that are particularly suitable for determining acetyl-lysine status include those known by one skilled in the art (see e.g., Hebert, A. S., et al., Mol. Cell. 49:186-199 (2013)).

The diseases and disorders associated with a deficiency in frataxin can be, for example, Friedereich's Ataxia, Parkinson's Disease, Alzheimer's Disease, alcoholism, ischemic heart disease, dementia, Huntington's disease, Amyotrophic lateral sclerosis, cytochrome c oxidase deficiency, autosomal dominant progressive external ophthalmoplegia (ad-PEO), and Leber's Hereditary Optic Neuropathy (LHON). Particularly suitable samples may be a tissue having cells that possess mitochondria and may be from any part of the body that is affected by the disease. Particularly suitable tissues for obtaining samples can be, for example, liver, heart, white blood cells, and neural tissue.

In another aspect, the present disclosure is directed to a method of detecting the progression of a disease or a disorder associated with a deficiency in frataxin in a subject. The method includes measuring mitochondrial protein acetylation, especially lysine acetylation, in a first chronological sample and a second chronological sample from a subject having or suspected of having the disease or the disorder associated with a deficiency in frataxin. An increase in the mitochondrial protein acetylation in the second chronological sample indicates progression of the disease when compared to mitochondrial protein acetylation in the first chronological sample. For chronological measurement to detect the progression of a disease, mitochondrial protein acetylation can be determined from about one day to about 30 days. It is within the skill of those in the art to detect the progression of a mitochondrial respiratory chain disorder by measuring mitochondrial protein acetylation.

In another aspect, the present disclosure is directed to a method of monitoring the effectiveness of a therapy in a subject having or suspected of having a disease or a disorder associated with a deficiency in frataxin. The method includes measuring mitochondrial protein acetylation in at least a first chronological sample, administering the therapy to the subject and measuring mitochondrial protein acetylation in at least a second chronological sample from the subject. A decrease in the mitochondrial protein acetylation in the second chronological sample indicates effectiveness of therapy when compared to the mitochondrial protein acetylation in the first chronological sample. For chronological measurement to monitor the effectiveness of a mitochondrial respiratory chain disorder therapy, mitochondrial protein acetylation can be determined from about one day to about one year. It is within the skill of those in the art to begin a therapy and monitor the effectiveness of over the entire course of therapy, as well as for a time following termination of therapy.

In another aspect, the present disclosure is directed to a method for screening for agents that can be used as therapeutic agents for treating a disease or a disorder associated with a deficiency in frataxin. The method includes measuring mitochondrial protein acetylation in a subject having hyperacetylated mitochondrial proteins, administering an agent suspected of modulating protein acetylation to the subject, and measuring mitochondrial protein acetylation after administration of the agent. The agent is considered to be a candidate for treating the disease or the disorder associated with a deficiency in frataxin if the mitochondrial protein acetylation is decreased in the sample after administration of the agent.

In another aspect, the present disclosure is directed to a method of screening for a disease or a disorder associated with a deficiency in frataxin in a subject. The method includes determining the mitochondrial NADH level in a sample tissue, wherein an increase in NADH level in the sample tissue as compared to NADH level in normal tissue is indicative of a mitochondrial respiratory chain disorder.

The method may further include determining mitochondrial NADH level a sample tissue, determining $NAD^+$/NADH ratio in the sample tissue, determining mitochondrial $NAD^+$ level in a normal tissue, and determining $NAD^+$/NADH ratio in the normal tissue, wherein a decrease in the $NAD^+$/NADH ratio in the sample tissue as compared to the $NAD^+$/NADH ratio in normal tissue is indicative of a disease or a disorder associated with a deficiency in frataxin.

$NAD^+$ and NADH levels can be done using methods known by those skilled in the art using commercially available assays (Bioassay Systems). Once $NAD^+$ and NADH levels are determined, the $NAD^+$/NADH ratio can be calculated.

In another aspect, the present disclosure is directed to a kit for measuring or detecting mitochondrial protein acetylation. The kit may include reagents for processing a sample, for isolating mitochondria, and for detecting protein acetylation levels (e.g., isolation buffers, colorimetric assay buffers and reagents, and acetylation detection buffers and reagents). In one embodiment, the kit measures acetyl-lysine residues with, for example, an anti-acetyl-lysine-specific antibody. Suitable anti-acetyl-lysine antibodies are commercially available (Immumechem; Cell Signaling).

The kit may further use a combination of antibodies such as, for example, an anti-acetyl-lysine-specific antibody and an anti-mitochondrial protein antibody. Suitable anti-mitochondrial protein antibodies can be, for example, antibodies that specifically bind to NADH dehydrogenase [ubiquinone] 1 alpha subcomplex subunit 9 (NDUFA9), antibodies that specifically bind to acetyl-CoA synthetase 2 (AceCS2), antibodies that specifically bind to frataxin, antibodies that specifically bind to complex II 30 kDa subunit, antibodies that specifically bind to complex III Rieske protein, antibodies that specifically bind to NAD-dependent deacetylase sirtuin-3 (SIRT3), antibodies that specifically bind to voltage-dependent anion-selective channel (VDAC) and antibodies that specifically bind to other mitochondrial proteins known to those skilled in the art. The antibodies may be, for example, monoclonal antibodies, polyclonal antibodies and combinations thereof.

Kits may also use solid supports such as, for example, microtiter plates, membranes (e.g., nitrocellulose, polyvinyl chloride, nylon, polyvinylidine fluoride, diazotized paper) and beads (e.g., polystyrene latex, activated beads, Protein A beads, Protein G beads).

The kit can further include instructions for using the reagents for processing a sample, for isolating mitochondria, for measuring mitochondrial protein acetylation, for detecting protein acetylation levels and combinations thereof. The instructions may be provided in the kit packaging and provided by other media such as, for example, a website.

The disclosure will be more fully understood upon consideration of the following non-limiting Examples.

EXAMPLE

Example 1

Materials and Methods

Frataxin Conditional Knockout Mouse Breeding and Genotyping.

Mice were obtained from Helene Puccio and bred as described previously to generate the NSE and MCK-Cre conditional knockout animals. PCR was used to detect the presence of a 500 bp product of exon 4 and a 790 bp product of the Cre transgene for genotyping. Mice that were genotyped as $Frda^{L3/\Delta}$, Cre+ represent the conditional knockout animals.

Mouse Tissue Preparation.

For the isolation of whole heart homogenate, animals were sacrificed by $CO_2$ asphyxiation and the tissue was immediately excised, washed and minced in cold phosphate-buffered saline. The tissue was then placed in 1-2 ml of ice-cold complete RIPA buffer containing an EDTA-free protease inhibitor cocktail (Roche product #05056489001), and 10 mM nicotinamide (NAM), 200 nM Trichostatin A, and 5 mM sodium butyrate as deacetylase inhibitors. The tissues were then homogenized with at least 10 passes of a motor-driven Potter-Elvehjem homogenizer at high speed. The whole tissue homogenates were then transferred to 1.5 ml tubes and spun at 17,000×g for 10 min at 4° C. in a desktop centrifuge to pellet membranes and tissue debris. The supernatant was saved and immediately frozen on dry-ice and stored at −80° C. for later analysis. Frozen, RIPA buffer solubilized ANT1$^{-/-}$ and COI missense mutation cardiac lysates were provided by Dr. Douglas C. Wallace of The Children's Hospital of Philadelphia.

Isolation of Cardiac Mitochondria.

Wild-type or frataxin conditional KO mice were sacrificed by $CO_2$ asphyxiation and their hearts were immediately removed and submerged in ice-cold mitochondrial isolation buffer (MIB) containing 220 mM mannitol, 70 mM sucrose, 30 mM Tris-Cl (pH 7.4), 0.5 mM EGTA, and 0.1% BSA. Heart tissue was minced and washed in MIB to eliminate blood and serum contaminants, then quickly weighed. Minced heart tissue from 2-3 animals was submerged in 3 ml/g MIB containing an EDTA-free protease inhibitor cocktail (Roche) and 10 mM nicotinamide (NAM), 200 nM Trichostatin A, and 5 mM sodium butyrate as deacetylase inhibitors. Heart tissue was homogenized with four passes of a motor-driven Potter-Elvehjem homogenizer with a Teflon pestle at medium speed on ice. An additional 7 ml/g MIB was added to the heart homogenate, which was then transferred to a pre-chilled 50 ml conical tube. A crude mitochondrial pellet was obtained via a standard differential centrifugation method. Briefly, nuclei and the heavy cell fraction are removed via centrifugation for 15 minutes at 1000×g at 4° C. The resulting post-nuclear supernatant was subjected to centrifugation for 15 min at 10,000×g to pellet mitochondria. The supernatant was removed as the cytosolic fraction and sedimented mitochondria were gently resuspended in 1 ml ice-cold MIB containing deacetylase inhibitors and then diluted with MIB to a total volume of 10 ml and centrifuged again for 15 min at 10,000×g. The supernatant was then removed and sedimented mitochondria are gently washed in 0.5 M KCl to remove endoplasmic reticulum and lysosome contaminants. For Western blotting, the sedimented mitochondria were solubilized in complete RIPA buffer containing protease and deacetylase inhibitors (see Mouse tissue preparation) and frozen until later analysis. For immunoprecipitations, the pelleted mitochondria were resuspended in ice-cold buffer containing 50 mM Tris-Cl (pH 7.4), 150 mM NaCl, and an EDTA-free protease inhibitor tablet and immediately frozen at −80° C. For NAD$^+$ and NADH measurements, sedimented mitochondria were immediately resuspended in 180 µl of ice-cold 1 mM Tris-Cl pH 7.4, 150 mM NaCl and extracted appropriately (see Mitochondrial NAD$^+$ and NADH measurements).

Antibodies and Western Blotting.

Antibodies used included anti-acetyl-lysine (Immunechem anti-acetyl-lysine (Cell Signaling) anti-complex II 30 kDa subunit, anti-NDUFA9, anti-complex III Rieske protein (Mitosciences), anti-SIRT3 (provided by E. Verdin, Gladstone Institute, UCSF), anti-frataxin (provided by G. Isaya, Mayo Clinic), anti-SIRT3 D22A3, anti-VDAC D73D12, and anti-histone H3 (Cell Signaling), anti-GAPDH and anti-tubulin (Sigma), and anti-AceCS2 (ACSS1)(Abcam). Following transfer of the SDS-PAGE gel proteins to nitrocellulose membranes, the membrane was blocked for 45 min in PBS-0.05% Tween-20 supplemented with 5% non-fat dry milk. Signals were visualized with SuperSignal West chemiluminescent substrate (Thermo-Pierce). Western blot signal intensities were determined by density quantification using ImageJ software where appropriate. Protein concentrations were determined using the BCA method (Pierce).

Immunoprecipitation of Acetyl-Lysine Proteins.

For immunoprecipitation of acetyl-lysine proteins and detection of NDUFA9 and AceCS2 acetylation, 500 µg to 1 mg of cardiac mitochondria was solubilized for 30 min on ice in 1% lauryl maltoside (Mitosciences) and centrifuged at 16,000×g for 10 min at 4° C. to pellet debris and lipid membrane components. Anti-acetyl-lysine antibody (Cell Signaling) was loaded with the solubilized mitochondrial supernatant at a ratio of 1:25 w/w and incubated overnight at 4° C. with gentle agitation. Following incubation with the anti-acetyl-lysine antibody, the sample was incubated at 4° C. with gentle agitation for an additional 2 hours with 7.5 µl Protein A agarose (Invitrogen) plus 7.5 µl Protein G agarose (Roche). Agarose was collected via a 1 min centrifugation at 400×g at 4° C. with a desktop centrifuge and the unbound mitochondrial supernatant was carefully removed from above the agarose beads. The beads were washed 3 times for 5 min. in 500 µl IP buffer containing 50 mM Tris-Cl (pH 7.4), 150 mM NaCl, 1 mM EGTA, and 0.5% NP-40 at 4° C. and then incubated in 30 µl SDS sample loading buffer and boiled at 95° C. for 5 min. The immunoprecipitated sample was then resolved on a 12% SDS-PAGE and processed for Western blotting.

Mitochondrial NAD$^+$ and NADH Measurements.

NAM was excluded from MIB used to isolate mitochondria for NAD$^+$ measurements as the enzyme nicotinamide phosphoribosyltransferase (Nampt) catalyzes the formation of NMN, an NAD$^+$ precursor, from NAM. NAD(H) measurements were performed with a cycling assay according to the manufacturer's instructions (Bioassay Systems). NAD$^+$ was extracted in the mitochondrial sample via addition of strong acid and then heated at 60° C. to eliminate the presence of the reduced nucleotide (NADH). NADH was extracted in mitochondrial sample homogenate via addition of strong base and then heated at 60° C. to eliminate the presence of the oxidized nucleotide (NAD$^+$). The extractions were neutralized with the opposite extraction buffer and the dehydrogenase cycling assay was performed in which, in the presence of lactate, lactate dehydrogenase, diaphorase and MTT formazan reagent, the concentration of NAD$^+$ or NADH present in the sample is proportional to the amount of reduced MTT formation which was colorimetrically detected with a plate reader at 562 nm. Sample concentrations were determined via an NAD$^+$ standard curve. The coenzyme concentration was normalized to the protein concentration of the sample.

In Vitro SIRT3 Deacetylation Assay.

200 µl of 2 µg/µl Frataxin$^{-/-}$ cardiac mitochondria frozen in 50 mM Tris-Cl (pH 7.4). 1.50 mM NaCl was thawed on ice and solubilized in 1% lauryl maltoside for 30 min on ice and centrifuged at 16,000×g for 10 min at 4° C. to pellet debris and lipid membrane components. 15 µl of the soluble mitochondrial supernatant was mixed 1:1 with 15 µl of 2× deacetylase buffer (50 mM Tris-Cl pH 8.0, 150 mM NaCl, 2 mM MgCl$_2$, with or without 20 mM NAD$^+$). 3 µg of recombinant GST-tagged SIRT3 corresponding to amino acids 101-399 of human SIRT3 (Sigma) in 40 mM Tris-Cl pH 8.0, 240 mM NaCl, and 20% glycerol was added to 30 µl (30 µg) of the 1:1 mitochondrial protein:2× deacetylase buffer mix in a 1.5 ml tube. An appropriate amount of buffer containing only 40 mM Tris-Cl, 240 mM NaCl, and 20% glycerol was added to incubations lacking SIRT3 to equalize the incubation volumes and conditions. The reactions were incubated for 4 hours at 37° C. at 400 rpm in an Eppendorf Thermomixer and briefly centrifuged every 30 min of incubation time to minimize reaction condensation. Following the incubation, the reactions were stopped upon addition of SDS loading buffer, boiled and processed for Western blotting as described previously.

Detection of 4-HNE Modified SIRT3.

For the detection of 4-HNE modified SIRT3, cardiac mitochondrial proteins were solubilized as described earlier and 4-HNE modified proteins were derivatized to a biotin group via a 2 hour incubation in 5 mM EZ-Link hydrazide biotin (Thermo Scientific) in the dark. The samples were dialyzed 1:10000 in PBS overnight to remove excess biotin hydrazide. 100 µg of protein sample was then incubated with 50 µl of NeutrAvidin Agarose Resin (Thermo Scientific) at 4° C. with gentle rocking overnight. Beads were washed 5 times for 5 mM with 500 µl PBS-0.2% Tween 20, then boiled at 95° C. in 35 µl SDS loading buffer and processed for Western blotting as described previously.

Statistical Analysis.

Statistical significance was determined using a two sample t-test assuming unequal variances. Any P value less than 0.05 was judged to be significant.

Example 2

In this Example, NSE- and MCK-Cre conditional mouse models for Friedreich's Ataxia (FRDA) were analyzed for protein acetyl-lysine modifications.

Figure 2:
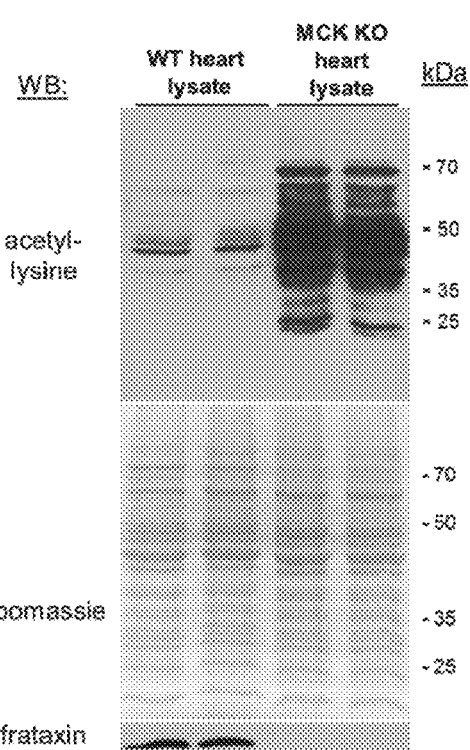
FIG. 2 is a Western blot (WB) probing for internal acetyl-lysine residues using total heart homogenates prepared from 9 week-old WT (n=2, lanes 1 and 2) and 9 and 11 week-old MCK-Cre mouse models of FA (lanes 3 and 4, respectively), the corresponding SDS-PAGE gel stained with Coomassie Blue and a Western blot probing for frataxin as discussed in Example 2.
Figure 3:
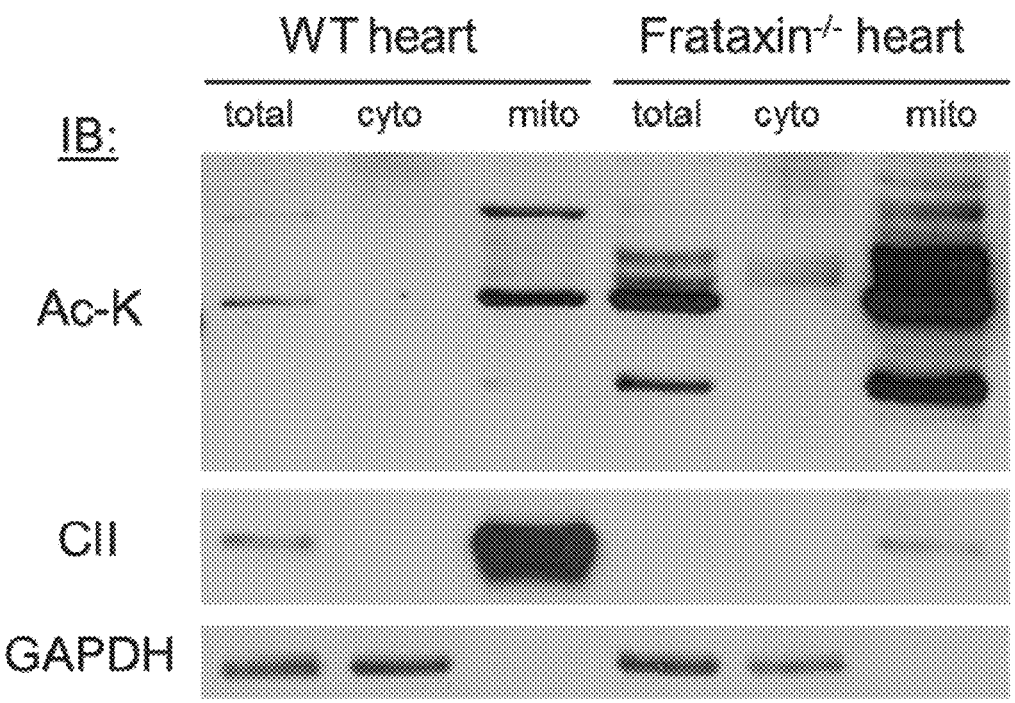
FIG. 3 is a Western Blot probing for internal acetyl-lysine residues ("Ac-K") of total heart homogenate ("total"), the cytoplasmic fraction ("cyto") and the mitochondrial ("mito") fraction, a Western blot probing for the mitochondrial marker complex II iron-sulfur subunit, and a Western blot probing for the cytoplasmic marker GAPDH as discussed in Example 2.
Figure 4:
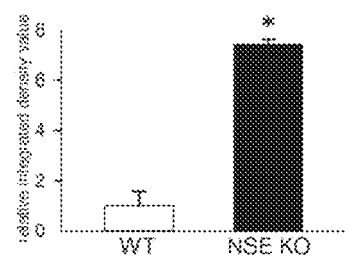
FIG. 4 is a graph showing the average relative integrated densitometry values from the acetyl-lysine Western blot in FIG. 1 (mean±SD; *P<0.05) as discussed in Example 2.
Figure 5:
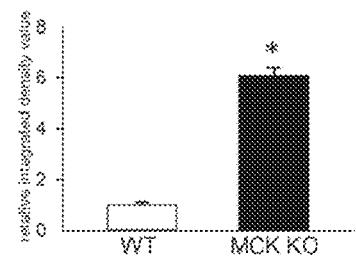
FIG. 5 is a graph showing the average relative integrated densitometry values from the acetyl-lysine Western blot in FIG. 2 (mean±SD; *P<0.05) as discussed in Example 2.

Specifically, whole heart lysates from wild-type (WT), NSE, and MCK conditional mouse models of FRDA were analyzed by Western blot analysis to assay protein acetyl-lysine modifications. As shown in FIGS. 1 and 2, heart lysates from both the NSE (NSE KO) and MCK (MCK KO) mouse models of FRDA exhibited marked increases in acetyl-lysine modifications as compared to age-matched control hearts. As demonstrated in FIG. 3, hyperacetylation was localized to cardiac mitochondria. As shown in FIGS. 4 and 5, the increases in acetyl-lysine modifications as compared to age-matched control hearts were statistically significant. The differences were most dramatic in proteins with an estimated molecular weight between approximately 30 and 75 kDa (FIGS. 1 and 2.)

Example 3

In this Example, sub-fractionation of heart samples was performed to determine the sub-cellular distribution of hyperacetylated proteins.

Analysis of the purity of these mitochondrial preparations using antibodies to Historic H3 (a cytoplasmic marker), Gapdh (a cytoplasmic marker), VDAC (a mitochondrial marker) and Complex II (a mitochondrial marker) showed that nuclear and cytosolic proteins were excluded and they were highly enriched for markers of both the outer and inner mitochondrial membranes (FIG. 6). Using day 24 wild-type (WT, n=2) control and NSE-Cre frataxin-deficient cardiac mitochondrial preparations (n=2), Western blot analysis was performed for acetyl-lysine modifications.

Figure 9:
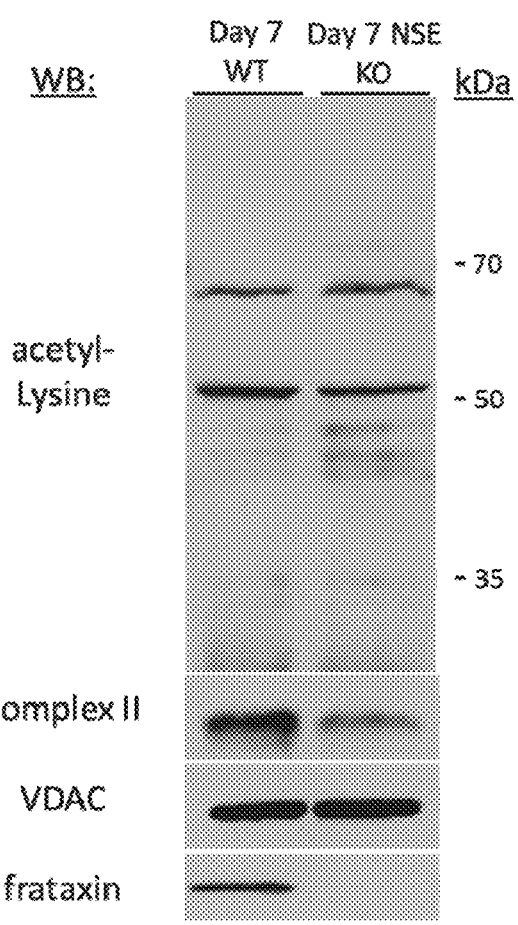
FIG. 9 is a Western blot probing for internal acetyl-lysine residues of mitochondrial protein preparations from WT or NSE-Cre frataxin knockout hearts at day 7 showing an increase in acetylation as early as post-natal day 7 concomitant with downregulation of the respiratory complex II iron-sulfur as discussed in Examples 3 and 4.

Control cardiac mitochondria exhibited several acetylated proteins detectable by Western blot. However, frataxin-deficient cardiac mitochondria displayed marked hyperacetylation of numerous proteins (FIGS. 3 and 7). This was accompanied by a characteristic downregulation of respiratory complex I and II (succinate dehydrogenase) that was present as early as 7 days post-natal (FIG. 9). Levels of the dominant mitochondria-localized $NAD^+$-dependent deacetylase SIRT3 displayed a mild, though insignificant, increase in frataxin-deficient mitochondrial preparations (FIGS. 7 and 8). These results indicated that the hyperacetylation observed at the level of whole cardiac lysate was predominantly localized to mitochondria.

Example 4

In this Example, the developmental profile of mitochondrial protein acetylation was determined.

Specifically, the NSE-Cre mouse models of FRDA begin to develop cardiac hypertrophy in the second week of life. Thus, cardiac mitochondria from WT control and NSE-Cre mice at post-natal days 7, 17, and 24 were prepared and analyzed by Western blot analysis.

Figure 10:
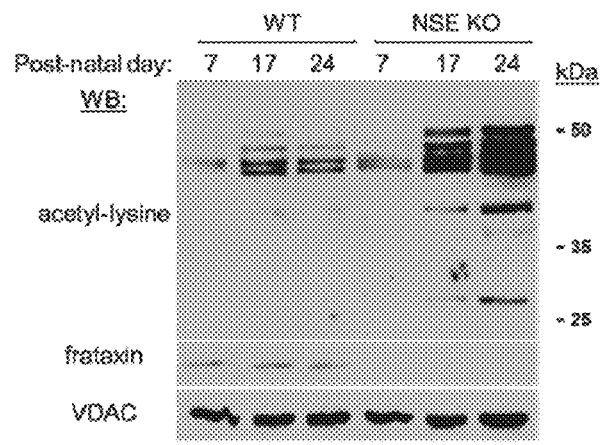
FIG. 10 is a Western blot probing for internal acetyl-lysine residues of mitochondrial protein preparations isolated from 2-3 WT or NSE-Cre frataxin knockout hearts at day 7, day 17, and day 24 in their post-natal development, a Western blot probing for frataxin and VDAC as a loading control as discussed in Example 4.
Figure 11:
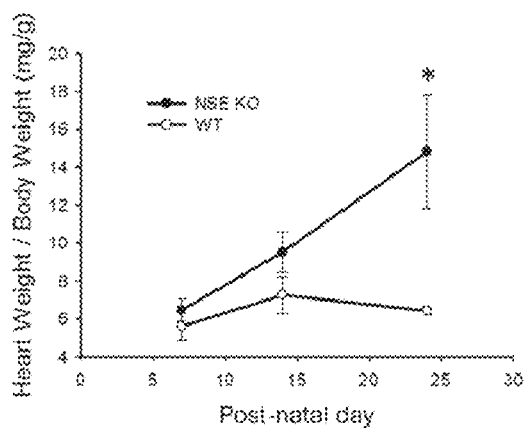
FIG. 11 is a graph assessing the post-natal development of cardiac hypertrophy in the NSE KO mice as measured by heart weight divided by body weight (mean±SD; n=3 measurements at each time point; *P<0.05) as discussed in Example 4.

As shown in FIGS. 9 and 10, at post-natal day 7, NSE-Cre cardiac mitochondrial proteins exhibited only a mildly increased acetylation state as compared to their wild-type (WT) counterparts. However, at post-natal day 17, NSE-Cre cardiac mitochondria displayed increased acetylation of cardiac mitochondrial proteins as compared to their WT counterparts, which became more dramatic by post-natal day 24. The progressive increase in cardiac mitochondrial protein acetylation over this time frame corresponded with the development of cardiac hypertrophy in the NSE-Cre models (FIG. 11).

Example 5

In this Example, the redox states of WT and frataxin deficient cardiac mitochondria preparations were determined.

Figure 12:
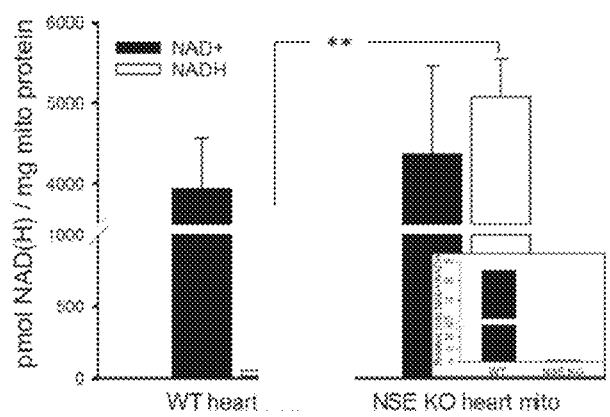
FIG. 12 is a graph showing the determination of nicotinamide adenine dinucleotide ($NAD^+$) and reduced $NAD^+$ (NADH) levels in WT and frataxin deficient cardiac mitochondrial preparations (n=3-5 biological replicates per condition, mean±SD; **P<0.005) and the figure inset shows the ratio of $NAD^+$ to NADH for WT and NSE-KO heart mitochondria as discussed in Example 5.

Individual measurements were performed on a pooled sample of at least 300 µg of fresh cardiac mitochondria derived from 2-3 hearts and normalized to total mitochondrial protein input. As shown in FIG. 12, WT heart mitochondria displayed robust $NAD^+$ levels and over 100-fold less NADH by comparison, which is consistent with highly oxidative cardiac catabolism and a continuous demand for carbon fuels. Frataxin deficient mitochondria displayed a mild, though insignificant, increase in $NAD^+$ levels when compared to WT. In contrast, frataxin deficient mitochondrial NADH levels were, on average, over 95-fold greater than in WT mitochondria (P<0.005) resulting in a corresponding $NAD^+$/NADH ratio that was 85-fold less than in WT animals (FIG. 12 inset). The observed accumulation of NADH and consequent shift in mitochondrial redox state is consistent with the impairments of mitochondrial respiration found in both human FRDA patients, and the NSE and MCK animal models.

Example 6

In this Example, differential modification of SIRT3 by 4-HNE in frataxin deficient cardiac mitochondria was determined.

Figure 13:
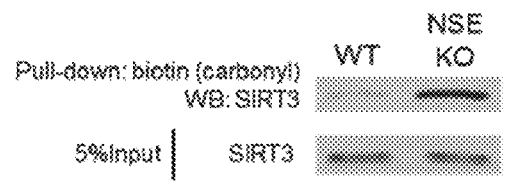
FIG. 13 is a Western blot showing the carbonyl pulldown of SIRT3 in frataxin-deficient mitochondria as discussed in Example 6.

Specifically, all reactive aldehyde containing mitochondrial proteins following their derivatization to biotin hydrazide were pulled down, and then analyzed by Western blot for SIRT3. As shown in FIG. 13, SIRT3 in WT heart mitochondria exhibited a small amount of 4-HNE modification. In contrast, SIRT3 in frataxin-deficient mitochondria exhibited a marked increase in 4-HNE modification suggesting that SIRT3 may be directly inhibited via carbonyl group adduction in the setting of frataxin deficiency.

Example 7

In this Example, the acetylation states of known targets of SIRT3-mediated deacetylation was determined.

Figure 14:
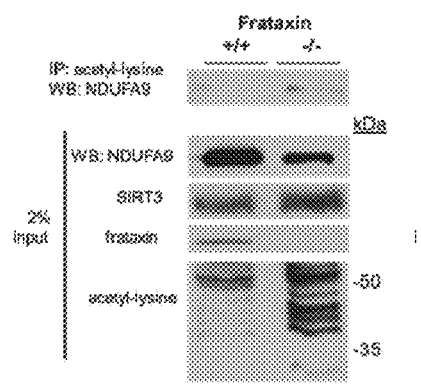
FIG. 14 is a Western blot showing immunoprecipitation of WT (+/+) and NSE-Cre frataxin-deficient (−/−) cardiac mitochondrial proteins with an acetyl-lysine antibody and subsequent Western blot probing for the respiratory complex I subunit NDUFA9 and Western blots of 2 percent of the total mitochondrial lysate input used for the immunoprecipitations showing NDUFA9, SIRT3, frataxin, and the acetylation states of both samples as discussed in Example 7.
Figure 15:
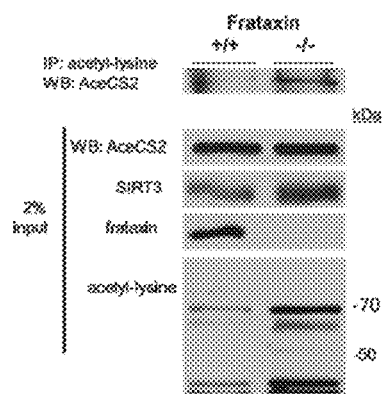
FIG. 15 is a Western blot showing immunoprecipitation of WT (+/+) and NSE-Cre frataxin-deficient (−/−) cardiac mitochondrial proteins with an acetyl-lysine antibody and subsequent Western blot probing for acetyl-CoA synthetase 2 (AceCS2) and Western blots of 2 percent of the total mitochondrial lysate input used for the immunoprecipitations showing AceCS2, SIRT3, frataxin, and the acetylation states of both samples as discussed in Example 7.

Mitochondrial acetyl-lysine proteins were immunoprecipitated and analyzed by Western blot for NDUFA9. Consistent with previous findings, a minimal amount of NDUFA9 acetyl-lysine signal in the WT (+/+) mitochondrial immunoprecipitate was observed. However, the frataxin-deficient (−/−) mitochondrial immunoprecipitate displayed a greater acetylated NDUFA9 signal despite downregulation of NDUFA9 as seen in the input (FIG. 14). The acetylation state of acetyl-CoA synthetase 2 (AceCS2) was also analyzed. Similarly, this analysis revealed a greater amount of acetylated AceCS2 in the frataxin-deficient (−/−) condition as compared to the WT (+/+) (FIG. 15). The increased acetylation states of two known targets of SIRT3-mediated deacetylation indirectly demonstrated that SIRT3 is inhibited in frataxin-deficient cardiac mitochondria. Importantly, increases in the acetylation states of NDUFA9 and AceCS2 were linked to a decrease in the activity of respiratory complex I and the synthesis of activated acetate, respectively.

Example 8

In this Example, the rescue of inhibited endogenous SIRT3 by the addition of SIRT3 and $NAD^+$ in vitro was determined.

Figure 16:
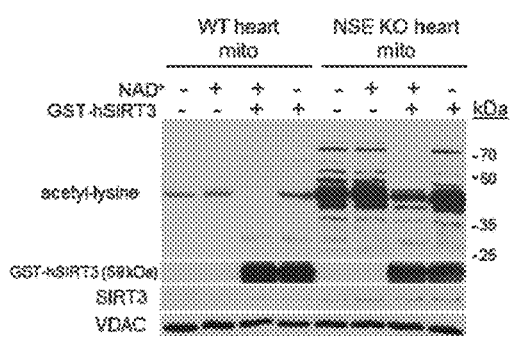
FIG. 16 shows Western blots probing for internal acetyl-lysine residues of mitochondrial protein preparations from WT or NSE-Cre frataxin knockout hearts incubated with recombinant SIRT3 and NAD$^+$ showing a reduction of the acetyl-lysine signal as discussed in Example 8.

Specifically, solubilized WT and frataxin-deficient cardiac mitochondrial proteins were incubated with glutathione S-transferase tagged, processed human recombinant SIRT3 (GST-hSIRT3) in the presence or absence of $NAD^+$ to assay for changes in acetylation states. Incubating solubilized WT or frataxin$^{-/-}$ cardiac mitochondrial homogenates with $NAD^+$ alone caused no change in acetylation signal. In contrast, incubating frataxin deficient mitochondrial protein with 3 μg of GST-hSIRT3 and $NAD^+$ resulted in a marked reduction of acetyl-lysine signal from nearly every protein band, while completely eliminating the acetyl-lysine signal of multiple bands (FIG. 16). Furthermore, the observed reduction in acetylation signal was abolished upon withdrawal of $NAD^+$ from the incubation buffer, demonstrating that the hyperacetylated protein lysine residues in frataxin-deficient cardiac mitochondria were specifically sensitive to $NAD^+$-dependent SIRT3-mediated deacetylation and that the observed hyperacetylation was not caused by a general increase in non-specific lysine acetylation. Taken together, these data strongly suggest that hyperacetylation in frataxin deficient mitochondria was due to both redox-state and lipid-peroxidation-mediated inhibition of endogenous SIRT3.

Example 9

In this Example, alterations in cardiac acetylation profiles of other mitochondrial disorders caused by respiratory chain defects were determined.

Whole cardiac lysates were obtained from the cytochrome oxidase I (COI) mouse model, which harbors a mtDNA mutation causing a defect of respiratory complex IV, and the adenine nucleotide translocase knockout (ANT1$^{-/-}$) mouse model, which models a non-respiratory chain defect with deficiency of ATP translocation. These mice model the human mitochondrial disorders, autosomal dominant progressive external ophthalmoplegia (adPEO) and Leber's Hereditary Optic Neuropathy (LHON), respectively, and both models develop cardiomyopathy.

Figure 17:
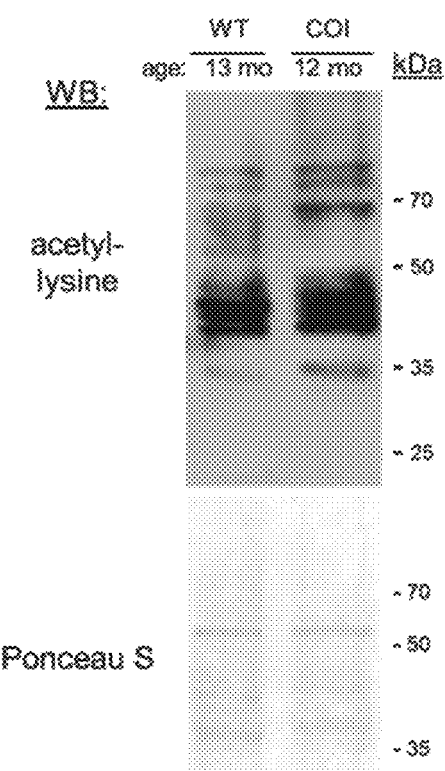
FIG. 17 is a Western blot probing for internal acetyl-lysine residues of whole heart lysate derived from a 13 month-old wild-type (WT) animal and a 12 month-old animal harboring a missense mutation in the mitochondrial genome-encoded protein subunit of the respiratory chain enzyme cytochrome c oxidase (COI) and the same membrane used for Western blotting stained with Ponceau S as discussed in Example 9.
Figure 18:
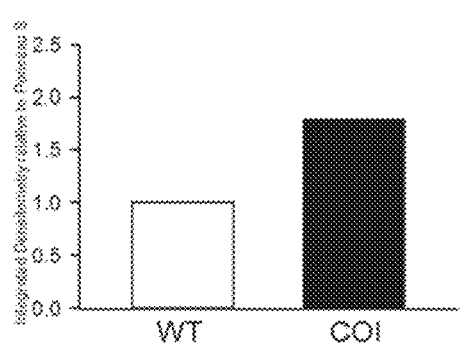
FIG. 18 is a graph showing the calculated integrated densitometry values for acetyl-lysine signal relative to Ponceau S signal from FIG. 17 as discussed in Example 9.
Figure 19:
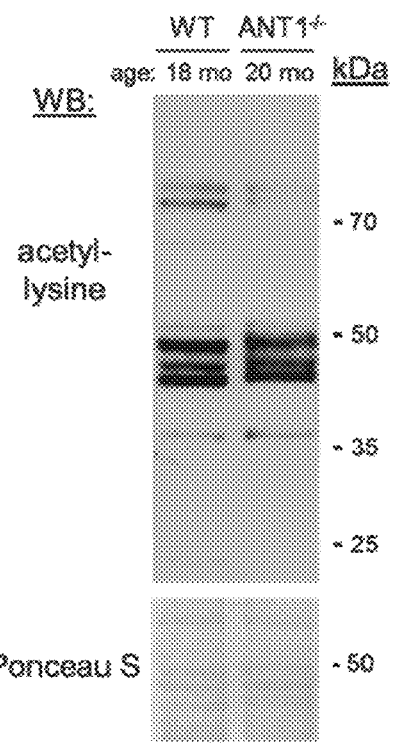
FIG. 19 is a Western blot probing for internal acetyl-lysine residues of whole heart lysate prepared from a 18 month-old WT animal and a 20 month-old animal lacking the non-respiratory chain mitochondrial inner membrane protein adenine nucleotide translocase 1 (ANT1$^{-/-}$) and the same membrane used for Western blotting stained with Ponceau S as discussed in Example 9.
Figure 20:
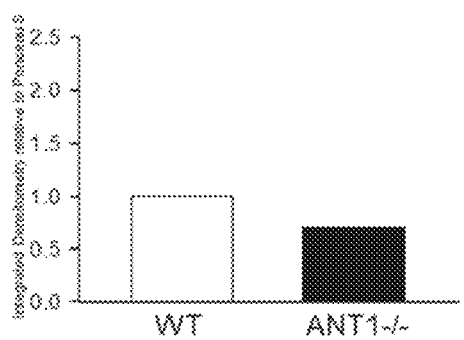
FIG. 20 is a graph showing the calculated integrated densitometry values for acetyl-lysine signal relative to Ponceau S signal from FIG. 19 as discussed in Example 9.

Western blot analysis of cardiac acetylation revealed mild to moderate increases in acetylation in 12 month old COI hearts as compared to 13 month-old control hearts (FIGS. 17 and 18). Interestingly, 20 month old ANT1$^{-/-}$ hearts exhibited a small decrease in acetyl-lysine profiles when compared to 18 month old control hearts (FIGS. 19 and 20). Taken together with data from the frataxin deficient mice, these results suggest that increases in protein acetylation may be a common feature of respiratory chain malfunction in the mammalian heart.

Example 10

In this Example, mitochondrial acetylation status in frataxin-deficient mice treated with TAT-Frataxin fusion protein was determined.

Figure 21A:
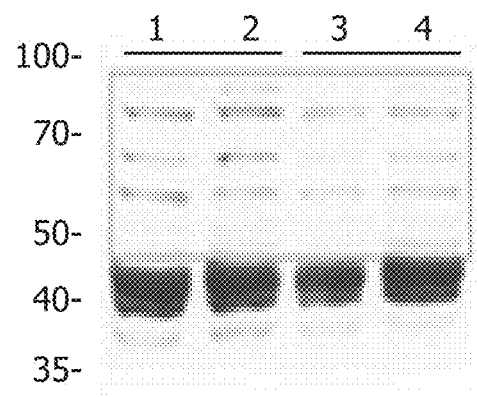
FIG. 21A is a Western blot probed for acetylation of mitochondrial proteins from mice with Friedreich's Ataxia treated with TAT-Frataxin as discussed in Example 10.

The TAT-Frataxin fusion protein was prepared as described in Vyas et al. (Hum. Mol. Genet. 2012, 21(6): 1230-1247). NSE-Cre Frataxin knockout mice (FXN$^{-/-}$) were treated with TAT-Frataxin for 2 weeks (FXN$^{-/-}$+TAT-FXN; FIG. 21A lanes 3 and 4) or phosphate buffered saline (FXN$^{-/-}$; FIG. 21A lanes 1 and 2). Specifically, mice were dosed according to body weight with a total volume of approximately 20 μl/gram of weight administered intraperitoneally. Whole heart lysate from 4 week old NSE-Cre FXN knockout mice was quantified and equal loading of each lane was verified by Coomassie staining. Western blots were probed with anti-acetyl lysine antibody and pixel intensity was quantified for the top 4 bands identified in lanes 1-4 of FIG. 21A.

Figure 21B:
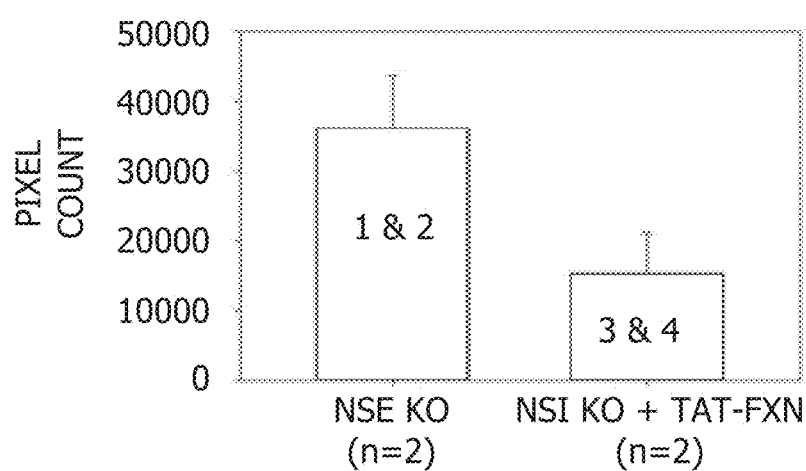
FIG. 21B is a graph quantifying the amount of acetylation of the upper most 4 bands shown in FIG. 21A by densitometry as discussed in Example 10.

As illustrated in FIG. 21B, treatment of mice TAT-Frataxin decreased protein acetylation in NSE-Cre FXN knockout mice (NSE KO+TAT-FXN). Therefore, mitochondrial protein acetylation status can be used as a biomarker to monitor treatment in a mouse knockout model of Friedreich's Ataxia, which is associated with a deficiency in frataxin.

The Examples described above demonstrate that a deficiency in frataxin can cause progressive hyperacetylation of mitochondrial proteins. More specifically, hyperacetylation of mitochondrial proteins may be due to the inhibition of a SIRT3 deacetylase. SIRT3 may respond to the flux of mitochondrial. $NAD^+$ and NADH, which is determined, in large part, by the capacity of the respiratory chain to oxidize NADH. This capacity is severely decreased in FRDA, as well as in other mitochondrial defects such as cytochrome c oxidase (complex IV) deficiency, causing an accumulation of NADH and, consequently, a redox state of perceived nutrient excess. It has now been discovered that hyperacetylation of numerous mitochondrial proteins correlates with the inhibition of the $NAD^+$-dependent SIRT3 deacetylase. This inhibition is caused by an 85-fold decrease in mitochondrial $NAD^+$/NADH ratio and direct carbonyl group modification of a NAD-dependent deacetylase. It has also been discovered that the inhibition may be rescued by the administration of a NAD-dependent deacetylase and $NAD^+$. It has further been discovered that protein hyperacetylation provides a specific biomarker of a deficiency in frataxin. Thus, loss of frataxin causes hyperacetylation of proteins because the respiratory chain is defective and the Krebs cycle.

In view of the above, it will be seen that the several advantages of the disclosure are achieved and other advantageous results attained. As various changes could be made in the above devices and methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A kit for measuring levels of mitochondrial protein acetylation comprising an anti-acetyl-lysine-specific antibody and an antibody that specifically binds to a mitochondrial protein wherein the mitochondrial protein is selected from the group consisting of NADH dehydrogenase [ubiquinone] 1 alpha subcomplex subunit 9 (NDUFA9), acetyl-CoA synthetase 2 (AceCS2), frataxin, complex II 30 kDa subunit, complex HI Rieske protein, NAD-dependent deacetylase sirtuin-3 (SIRT3), voltage-dependent anion-selective channel (VDAC), and combinations thereof.

2. The kit of claim 1 further comprising at least one of a reagent for processing a sample, a reagent for isolating mitochondria, and a reagent for measuring mitochondrial protein acetylation.

* * * * *